US010294174B2

(12) United States Patent
Ravishankar et al.

(10) Patent No.: US 10,294,174 B2
(45) Date of Patent: May 21, 2019

(54) CATALYST COMPOSITE AND PREPARATION THEREOF FOR ISOMERIZATION OF PARAFFINS

(71) Applicant: HINDUSTAN PETROLEUM COPORATION LTD., Mumbai (IN)

(72) Inventors: Raman Ravishankar, Karnataka (IN); Safinaz Saif, Karnataka (IN); Peddy Venkatachallapathy Rao, Karnataka (IN); Venkateswarlu Choudary Nettem, Karnataka (IN); Sriganesh Gandham, Viskhapatnam (IN)

(73) Assignee: Hindustan Petroleum Corporation Ltd., Mumbai (IN)

( * ) Notice: Subject to any disclaimer, the term of this patent is extended or adjusted under 35 U.S.C. 154(b) by 318 days.

(21) Appl. No.: 14/970,108

(22) Filed: Dec. 15, 2015

(65) Prior Publication Data

US 2017/0001924 A1    Jan. 5, 2017

(30) Foreign Application Priority Data

Jun. 30, 2015    (IN) .................. 2499/MUM/2015

(51) Int. Cl.
| | |
|---|---|
| C07C 5/27 | (2006.01) |
| B01J 27/19 | (2006.01) |
| B01J 27/188 | (2006.01) |
| B01J 37/04 | (2006.01) |
| B01J 37/08 | (2006.01) |
| B01J 23/42 | (2006.01) |
| B01J 23/755 | (2006.01) |
| B01J 21/18 | (2006.01) |

(52) U.S. Cl.
CPC ............. *C07C 5/2783* (2013.01); *B01J 21/18* (2013.01); *B01J 23/42* (2013.01); *B01J 23/755* (2013.01); *B01J 27/188* (2013.01); *B01J 27/19* (2013.01); *B01J 37/04* (2013.01); *B01J 37/08* (2013.01); *C07C 2521/18* (2013.01); *C07C 2523/42* (2013.01); *C07C 2523/755* (2013.01); *C07C 2527/188* (2013.01); *C07C 2527/19* (2013.01)

(58) Field of Classification Search
None
See application file for complete search history.

(56) References Cited

U.S. PATENT DOCUMENTS 6,610,195 B2 * 8/2003 Masloboishchikova .................... C07C 5/2724
208/136

OTHER PUBLICATIONS

Zheng et al., "Synthesis of biofuel via levulinic acid esterification over porous solid acid consisting of tungstophosphoric acid and reduced graphene oxide", Research on Chemical Intermediates, Nov. 2017, vol. 43, Issue 11, pp. 6651-6664. (Year: 2017).*

(Continued)

*Primary Examiner* — Melvin C. Mayes
*Assistant Examiner* — Stefanie J Cohen
(74) *Attorney, Agent, or Firm* — Robert L. Stearns; Dickinson Wright, PLLC

(57) ABSTRACT

A catalyst composition is provided for isomerization of paraffins comprising of at least one heteropoly acid and reduced graphene oxide. Further provided are a process for preparation of the catalyst composition and a process for isomerization of paraffins using the catalytic composition.

7 Claims, 4 Drawing Sheets

(56) References Cited

OTHER PUBLICATIONS

Nipane et al, reduced graphene oxide supported silicotungstic acid for efficient converstion of thiols to disulfides by hydrogen peroxide, Ind. Eng. Chem. Res, 53, pp. 3924-3930 (Year: 2014).*

Kim et al, polyoxometalate—reduced graphene oxide hybrid catalyst:, synthesis, structure and electrochemical properties, ACS Appl. Mater. Interfaces, 5, pp. 12197-12204 (Year: 2013).*

Yuan et al, solid acid-reduced graphene oxide nanohybrid for enhancing thermal stability, mechanical property and flame retardancy of polypropylene, RSC Adv, 2015, 5, pp. 41307-41316 (Year: 2015).*

* cited by examiner

CATALYST COMPOSITE AND PREPARATION THEREOF FOR ISOMERIZATION OF PARAFFINS

This U.S. Utility application claims priority to India Application No. 2499/MUM/2015, filed Jun. 30, 2015, and is incorporated herein by reference.

BACKGROUND OF THE INVENTION

1. Technical Field

The subject matter described herein relates in general to a catalyst composition for isomerization of paraffins comprising of at least one heteropoly acid and reduced graphene oxide. The invention also relates to a process for preparation of a catalyst composition for isomerization of paraffins. The invention further relates to a process for isomerization of paraffins using the catalytic composition.

2. Related Art

Graphene is a two-dimensional pure carbon sheet possessing remarkable strength, electrical and thermal conductivity. One atom thick graphene sheet may be obtained by chemical exfoliation of graphite by Hummer's Method or by chemical vapor deposition under controlled conditions. However graphene cannot be utilized as such because it is an unreactive and inert material without proper functionalization, on the other hand, reduced graphene oxide (rGO) is a reduced form of oxygenated graphene and is expected to be a very promising material to be used as a support in catalytic transformations owing to its remarkable properties such as high surface area, mechanical strength and thermal conductivity along with the potential to be utilized in the form of various nano and meso scale structures. The reduced graphene oxide sheets thus, can be functionalized and used as support for different organic transformations (Guerra et al., Appl. Catal A: Gen 2013; 468:474 467).

Phosphomolybdic acid (PMA) belongs to the class of materials called heteropoly acids which exist in one of the Keggin, Dawson or other structural forms. It is a highly acidic material and exhibits some very interesting properties such as pseudo-liquid behavior (Kozhevnikov IV. Chem Rev 1998; 98:198-171.), utility as catalyst in both homogeneous and heterogeneous phase (Kozhevnikov IV. J. Mol. Catal A: Chem 2007; 262:92-86.), low temperature activity and reversible structure evolution in the presence of water up to certain temperatures (Micek-Ilnicka A. J Mol. Catal A: Chem 2009; 308:14-1.) However PMA is a bulk material with very low surface area ($<5$ m$^2$/g) and low mechanical strength thereby limiting its applications. Recently, high resolution in situ and ex situ TEM studies have indicated that the crystallite size of platinum governs the nature of carbon deposited over the support as graphene sheets or carbon nanotubes (Peng et al., J. Catal. 2012; 286:29-22).

Monofunctional hybrid materials based on Keggin-type heteropolyacids supported on mesostructured silica were used in isomerization of n-hexane. The heteropolyacids, namely $H_3PW_{12}O_{40}$ or $H_4SiW_{12}O_{40}$, were immobilized onto SBA-15 type silica by incipient wetness impregnation. The resulting catalysts were thoroughly characterized by $N_2$ adsorption-desorption isotherms, XRD, $^{31}$P NMR, TGA and FT-IR. These hybrid materials were active for the gas-phase isomerization of n-hexane (Pinto et al., Applied Catalysis A: General 483 (2014): 103-109.). In another study, isomerization of n-butane in the presence of hydrogen catalyzed by a bifunctional catalyst consisting of Pt and $Cs_{2.5}H_{0.5}PW_{12}O_{40}$ was examined mostly at 573 K. (Kyutae, et al., Journal of Molecular Catalysis A: Chemical 115.3 (1997): 449-455.)

Jin et al. reported a series of Ni—$Cs_xH_{3-x}PW_{12}O_{40}/SiO_2$ catalysts which were prepared by direct synthesis method and characterized by BET, XRD, in situ XRD, FT-IR, $NH_3$-TPD, $H_2$-TPR, and $H_2$-TPD. The catalytic performance of the catalysts for the hydrocracking of n-decane with various concentrations of thiophene and pyridine was studied. (Jin, Hao, et al., Fuel 112 (2013): 134-139.)

In another study, Cs-exchanged phosphotungstic acids ($Cs_xH_{3-x}PW_{12}O_{40}$, x=1-3) were examined as a catalyst for the hydrocracking of extra-heavy oil (vacuum residue, API gravity=2.3°). (Eom, Hee-Jun, et al., Fuel 126 (2014): 263-270.)

SUMMARY

In an aspect of the present disclosure, there is provided a catalyst composition comprising at least one heteropoly acid and reduced graphene oxide.

In an aspect of the present disclosure, there is provided a process for producing a catalyst composition, the process comprising; contacting at least one heteropoly acid with reduced graphene oxide to obtain a first solution; stirring the first solution to obtain a second solution; drying the second solution to obtain a dried paste; calcining the dried paste to obtain a catalyst composition.

In an aspect of the present disclosure, there is provided a process for isomerization of paraffins comprising contacting the paraffins and hydrogen with a catalyst composition in a reactor; wherein the catalyst composition comprises of at least one heteropoly acid in an amount in the range of 9% to 91% w/w of the total weight of the composition; and reduced graphene oxide acid in an amount in the range of 9% to 91% w/w of the total weight of the composition.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION

Figure 1:
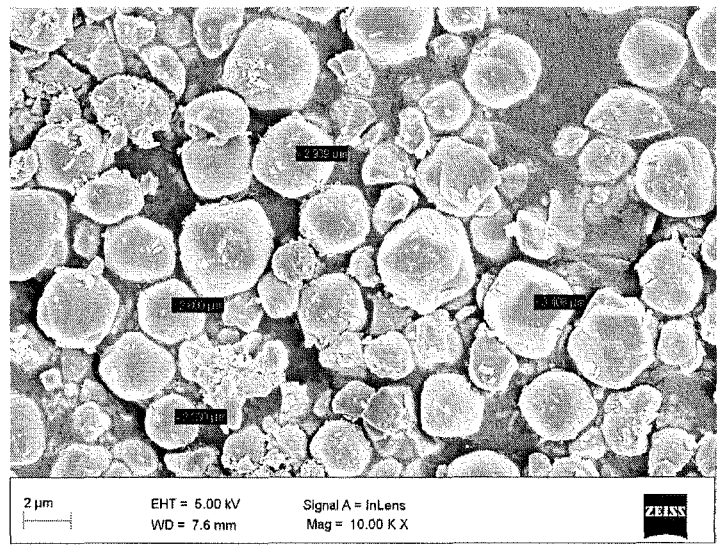
FIG. 1 depicts the scanning electron microscopy (SEM) image of conventional molybdophosphoric acid (MPA).

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "catalyst composite(s)" and "catalyst composition(s)" are used interchangeably in the present disclosure.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

In an embodiment of the present disclosure, there is provided a catalyst composition comprising at least one heteropoly acid and reduced graphene oxide.

In an embodiment of the present disclosure, there is provided a catalyst composition as described herein, wherein at least one heteropoly acid is in an amount in the range of 9% to 91% w/w of the total weight of the composition; and reduced graphene oxide is in an amount in the range of 9% to 91% w/w of the total weight of the composition.

In an embodiment of the present disclosure, there is provided a catalyst composition as described herein, wherein the at least one heteropoly acid is selected from the group consisting of tungstophosphoric acid (TPA), molybdophosphoric acid (MPA), and combinations thereof.

In an embodiment of the present disclosure, there is provided a catalyst composition as described herein, wherein the at least one heteropoly acid is in an amount in the range of 15% to 85% w/w of the total weight of the composition.

In an embodiment of the present disclosure, there is provided a catalyst composition as described herein, wherein the at least one heteropoly acid is in an amount in the range of 15% to 30% w/w of the total weight of the composition.

In an embodiment of the present disclosure, there is provided a catalyst composition as described herein, wherein the at least one heteropoly acid is in an amount in the range of 20% to 25% w/w of the total weight of the composition.

In an embodiment of the present disclosure, there is provided a catalyst composition as described herein, wherein the at least one heteropoly acid is tungstophosphoric acid (TPA) in an amount in the range of 15% to 85% w/w of the total weight of the composition.

In an embodiment of the present disclosure, there is provided a catalyst composition as described herein, wherein the at least one heteropoly acid is tungstophosphoric acid (TPA) in an amount in the range of 15% to 30% w/w of the total weight of the composition.

In an embodiment of the present disclosure, there is provided a catalyst composition as described herein, wherein the at least one heteropoly acid is tungstophosphoric acid (TPA) in an amount in the range of 20% to 25% w/w of the total weight of the composition.

In an embodiment of the present disclosure, there is provided a catalyst composition as described herein, wherein the at least one heteropoly acid is molybdophosphoric acid (MPA) in an amount in the range of 15% to 85% w/w of the total weight of the composition.

In an embodiment of the present disclosure, there is provided a catalyst composition as described herein, wherein the at least one heteropoly acid is molybdophosphoric acid (MPA) in an amount in the range of 15% to 30% w/w of the total weight of the composition.

In an embodiment of the present disclosure, there is provided a catalyst composition as described herein, wherein the at least one heteropoly acid is molybdophosphoric acid (MPA) in an amount in the range of 20% to 25% w/w of the total weight of the composition.

In an embodiment of the present disclosure, there is provided a catalyst composition as described herein, wherein the at least one heteropoly acid has a general formula selected from the group consisting of $H_xA_y[BD_6O_{24}].zH_2O$, $H_xA_y[BD_{12}O_{40}].zH_2O$, $H_xA_y[B_2D_{18}O_{62}].zH_2O$, and $H_xA_y[B_5D_{30}O_{110}].zH_2O$, wherein A is selected from a group consisting of alkali metal, alkali earth metal, post transitional metal, ammonium salt, and phosphonium salt; B is selected from a group consisting of P, Si, As, Ge, and D; D is selected from the group consisting of Ti, V, Cr, Mn, Fe, Co, Ni, Cu, Zn, Ga, Zr, Nb, Mo, Tc, Rh, Cd, In, Sn, Ta, W, and Re.

In an embodiment of the present disclosure, there is provided a catalyst composition as described herein, wherein the at least one heteropoly acid has a general formula of $H_{3-y}A_yPW_{12}O_{40}$, wherein y is 0 to 3, A is selected a group consisting of Li, Na, K, Rb, Cs, Mg, Ca, Al, ammonium salt, phosphonium salt, Pd, Ag, Ni, Al, and Cu.

In an embodiment of the present disclosure, there is provided a catalyst composition as described herein, wherein the reduced graphene is in an amount in the range of 15% to 85% w/w of the total weight of the composition.

In an embodiment of the present disclosure, there is provided a catalyst composition as described herein, wherein the reduced graphene is in an amount in the range of 70% to 85% w/w of the total weight of the composition.

In an embodiment of the present disclosure, there is provided a catalyst composition as described herein, wherein the reduced graphene is in an amount in the range of 70% to 80% w/w of the total weight of the composition.

In an embodiment of the present disclosure, there is provided a catalyst composition as described herein, the at least one heteropoly acid is in an amount in the range of 9% to 91% w/w of the total weight of the composition and is selected from the group consisting of tungstophosphoric acid (TPA), molybdophosphoric acid (MPA), and combinations thereof; and the reduced graphene oxide is in an amount in the range of 9% to 91% w/w of the total weight of the composition.

In an embodiment of the present disclosure, there is provided a catalyst composition as described herein, the at least one heteropoly acid is in an amount in the range of 15% to 30% w/w of the total weight of the composition and is selected from the group consisting of tungstophosphoric acid (TPA), molybdophosphoric acid (MPA), and combinations thereof; and the reduced graphene oxide is in an amount in the range of 70% to 85% w/w of the total weight of the composition.

In an embodiment of the present disclosure, there is provided a catalyst composition as described herein, the at least one heteropoly acid is in an amount in the range of 20% to 30% w/w of the total weight of the composition and is selected from the group consisting of tungstophosphoric acid (TPA), molybdophosphoric acid (MPA), and combinations thereof; and the reduced graphene oxide is in an amount in the range of 70% to 80% w/w of the total weight of the composition.

In an embodiment of the present disclosure, there is provided a catalyst composition as described herein, the at least one heteropoly acid is in an amount in the range of 9% to 91% w/w of the total weight of the composition and has a general formula selected from the group consisting of $H_xA_y[BD_6O_{24}].zH_2O$, $H_xA_y[BD_{12}O_{40}].zH_2O$, $H_xA_y[B_2D_{18}O_{62}].zH_2O$, and $H_xA_y[B_5D_{30}O_{110}].zH_2O$, wherein A is selected from a group consisting of alkali metal, alkali earth metal, post transitional metal, ammonium salt, and phosphonium salt; B is selected from a group consisting of P, Si, As, Ge, and D; D is selected from the group consisting of Ti, V, Cr, Mn, Fe, Co, Ni, Cu, Zn, Ga, Zr, Nb, Mo, Tc, Rh, Cd, In, Sn, Ta, W, and Re, and the reduced graphene oxide is in an amount in the range of 9% to 91% w/w of the total weight of the composition.

In an embodiment of the present disclosure, there is provided a catalyst composition as described herein, the at least one heteropoly acid is in an amount in the range of 9% to 91% w/w of the total weight of the composition and has a general formula selected a group consisting of $H_xA_y[BD_6O_{24}].zH_2O$, $H_xA_y[BD_{12}O_{40}].zH_2O$, $H_xA_y[B_2D_{18}O_{62}].zH_2O$, and $H_xA_y[B_5D_{30}O_{110}].zH_2O$, wherein A is selected a group consisting of Li, Na, K, Rb, Cs, Mg, Ca, Al, ammonium salt, phosphonium salt, Pd, Ag, Ni, Al, and Cu; B is selected from a group consisting of P, Si, As, Ge, and D; D is selected from the group consisting of Ti, V, Cr, Mn, Fe, Co, Ni, Cu, Zn, Ga, Zr, Nb, Mo, Tc, Rh, Cd, In, Sn, Ta, W, and Re, and the reduced graphene oxide is in an amount in the range of 9% to 91% w/w of the total weight of the composition.

In an embodiment of the present disclosure, there is provided a catalyst composition as described herein, the at least one heteropoly acid is in an amount in the range of 9% to 91% w/w of the total weight of the composition and has a general formula of $H_{3-y}A_yPW_{12}O_{40}$, wherein y is 0 to 3, A is Ni, and the reduced graphene oxide is in an amount in the range of 9% to 91% w/w of the total weight of the composition.

In an embodiment of the present disclosure, there is provided a catalyst composition as described herein, the at least one heteropoly acid is in an amount in the range of 20% to 30% w/w of the total weight of the composition and has a general formula of $H_{3-y}A_yPW_{12}O_{40}$, wherein y is 0 to 3, A is Ni, and the reduced graphene oxide is in an amount in the range of 70% to 80% w/w of the total weight of the composition.

In an embodiment of the present disclosure, there is provided a catalyst composition as described herein, the at least one heteropoly acid is in an amount in the range of 15% to 85% w/w of the total weight of the composition and is selected from the group consisting of tungstophosphoric acid (TPA), molybdophosphoric acid (MPA), and combinations thereof; and the reduced graphene oxide is in an amount in the range of 15% to 85% w/w of the total weight of the composition.

In an embodiment of the present disclosure, there is provided a catalyst composition as described herein, the at least one heteropoly acid is in an amount in the range of 15% to 85% w/w of the total weight of the composition and has a general formula selected from the group consisting of $H_xA_y[BD_6O_{24}].zH_2O$, $H_xA_y[BD_{12}O_{40}].zH_2O$, $H_xA_y[B_2D_{18}O_{62}].zH_2O$, and $H_xA_y[B_5D_{30}O_{110}].zH_2O$, wherein A is selected from a group consisting of alkali metal, alkali earth metal, post transitional metal, ammonium salt, and phosphonium salt; B is selected from a group consisting of P, Si, As, Ge, and D; D is selected from the group consisting of Ti, V, Cr, Mn, Fe, Co, Ni, Cu, Zn, Ga, Zr, Nb, Mo, Tc, Rh, Cd, In, Sn, Ta, W, and Re, and the reduced graphene oxide is in an amount in the range of 15% to 85% w/w of the total weight of the composition.

In an embodiment of the present disclosure, there is provided a catalyst composition as described herein, the at least one heteropoly acid is in an amount in the range of 15% to 85% w/w of the total weight of the composition and has a general formula selected from the group consisting of $H_xA_y[BD_6O_{24}].zH_2O$, $H_xA_y[BD_{12}O_{40}].xH_2O$, $H_xA_y[B_2D_{18}O_{62}].zH_2O$, and $H_xA_y[B_5D_{30}O_{110}].zH_2O$, wherein A is selected a group consisting of Li, Na, K, Rb, Cs, Mg, Ca, Al, ammonium salt, phosphonium salt, Pd, Ag, Ni, Al, and Cu; B is selected from a group consisting of P, Si, As, Ge, and D; D is selected from the group consisting of Ti, V, Cr, Mn, Fe, Co, Ni, Cu, Zn, Ga, Zr, Nb, Mo, Tc, Rh, Cd, In, Sn, Ta, W, and Re, and the reduced graphene oxide is in an amount in the range of 15% to 85% w/w of the total weight of the composition.

In an embodiment of the present disclosure, there is provided a catalyst composition as described herein, the at least one heteropoly acid is in an amount in the range of 20% to 25% w/w of the total weight of the composition and has a general formula of $H_{3-y}A_yPW_{12}O_{40}$, wherein y is 0 to 3, A is Nickel, and the reduced graphene oxide is in an amount in the range of 75% to 80% w/w of the total weight of the composition.

In an embodiment of the present disclosure, there is provided a catalyst composition as described herein, the at least one heteropoly acid is a tungstophosphoric acid in an amount of 23-25% w/w of the total weight of the composition and has a general formula of $H_{3-y}A_yPW_{12}O_{40}$, wherein A is Ni and y is 2.5, and the reduced graphene oxide is in an amount of 70-80% w/w of the total weight of the composition.

In an embodiment of the present disclosure, there is provided a catalyst composition as described herein, the at least one heteropoly acid is a molybdophosphoric acid in an amount of 23-25% w/w of the total weight of the composition and has a general formula of $H_{3-y}A_yPW_{12}O_{40}$, wherein A is Ni and y is 2.5, and the reduced graphene oxide is in an amount of 70-80% w/w of the total weight of the composition.

In an embodiment of the present disclosure, there is provided a catalyst composition as described herein, wherein the catalyst is used for isomerization of paraffins.

In an embodiment of the present disclosure, there is provided a process for producing a catalyst composition as described herein, the process comprising contacting at least one heteropoly acid with reduced graphene oxide to obtain a first solution; stirring the first solution to obtain a second solution; drying the second solution to obtain a dried paste; calcining the dried paste to obtain a catalyst composition.

In an embodiment of the present disclosure, there is provided a process for producing a catalyst composition as described herein, wherein the first solution is stirred for 8-20 hours at 70-100° C.

In an embodiment of the present disclosure, there is provided a process for producing a catalyst composition as described herein, wherein the first solution is stirred for 12 hours at 85° C.

In an embodiment of the present disclosure, there is provided a process for producing a catalyst composition as described herein, wherein the dried paste is calcined at 200-400° C. for a period of 2-6 hours.

In an embodiment of the present disclosure, there is provided a process for producing a catalyst composition as described herein, wherein the dried paste is calcined at 300° C. for a period of 4 hours In an embodiment of the present disclosure, there is provided a process for producing a catalyst composition as described herein, wherein the at least one heteropoly acid is selected from the group consisting of tungstophosphoric acid (TPA), molybdophosphoric acid (MPA), and combinations thereof.

In an embodiment of the present disclosure, there is provided a process for producing a catalyst composition as described herein, wherein the at least one heteropoly acid has a general formula selected from the group consisting of $H_xA_y[BD_6O_{24}].zH_2O$, $H_xA_y[BD_{12}O_{40}].zH_2O$, $H_xA_y[B_2D_{18}O_{62}].zH_2O$, and $H_xA_y[B_5D_{30}O_{110}].zH_2O$, wherein A is selected from a group consisting of alkali metal, alkali earth metal, post transitional metal, ammonium salt, and phosphonium salt; B is selected from a group consisting of P, Si, As, Ge, and D; D is selected from the group consisting of Ti, V, Cr, Mn, Fe, Co, Ni, Cu, Zn, Ga, Zr, Nb, Mo, Tc, Rh, Cd, In, Sn, Ta, W, and Re.

In an embodiment of the present disclosure, there is provided a process for producing a catalyst composition as described herein, wherein the at least one heteropoly acid has a general formula $H_{3-y}A_yPW_{12}O_{40}$.

In an embodiment of the present disclosure, there is provided a process for producing a catalyst composition as described herein, wherein A is selected from the group consisting of Li, Na, K, Rb, Cs, Mg, Ca, Al, ammonium salt, phosphonium salt, Pd, Ag, Ni, Al, and Cu.

In an embodiment of the present disclosure, there is provided a process for producing a catalyst composition as described herein, wherein the at least one heteropoly acid has a general formula $H_{3-y}A_yPW_{12}O_{40}$, and wherein y is 0 to 3.

In an embodiment of the present disclosure, there is provided a process for producing a catalyst composition as described herein, wherein the at least one heteropoly acid has a general formula $H_{3-y}A_yPW_{12}O_{40}$, and wherein y is 2.5.

In an embodiment of the present disclosure, there is provided a process for isomerization of paraffins comprising contacting the paraffins and hydrogen with a catalyst composition in a reactor; wherein the catalyst composition comprises of at least one heteropoly acid in an amount in the range of 9% to 91% w/w of the total weight of the composition; and reduced graphene oxide in an amount in the range of 9% to 91% w/w of the total weight of the composition.

In an embodiment of the present disclosure, there is provided a process for isomerization of paraffins comprising contacting the paraffins and hydrogen with a catalyst composition in a reactor; wherein the catalyst composition comprises of at least one heteropoly acid in an amount in the range of 9% to 91% w/w of the total weight of the composition; and reduced graphene oxide in an amount in the range of 9% to 91% w/w of the total weight of the composition.

In an embodiment of the present disclosure, there is provided a process for isomerization of paraffins comprising contacting the paraffins and hydrogen with a catalyst composition in a reactor; wherein the catalyst composition comprises of at least one heteropoly acid in an amount in the range of 15% to 30% w/w of the total weight of the composition; and reduced graphene oxide in an amount in the range of 70% to 85% w/w of the total weight of the composition to obtain isoparaffins, olefins, naphthalenes, and aromatics.

In an embodiment of the present disclosure, there is provided a process for isomerization of paraffins comprising contacting the paraffins and hydrogen with a catalyst composition in a reactor; wherein the catalyst composition comprises of at least one heteropoly acid in an amount in the range of 20% to 30% w/w of the total weight of the composition; and reduced graphene oxide in an amount in the range of 70% to 80% w/w of the total weight of the composition to obtain isoparaffins selectively more than 20%.

In an embodiment of the present disclosure, there is provided a process for isomerization of paraffins comprising contacting the paraffins and hydrogen with a catalyst composition in a reactor; wherein the catalyst composition comprises of at least one heteropoly acid in an amount in the range of 20% to 30% w/w of the total weight of the composition; and reduced graphene oxide in an amount in the range of 70% to 80% w/w of the total weight of the composition to obtain naphthalenes selectively more than 20%.

In an embodiment of the present disclosure, there is provided a process for isomerization of paraffins comprising contacting the paraffins and hydrogen with a catalyst composition in a reactor; wherein the catalyst composition comprises of at least one heteropoly acid in an amount in the range of 20% to 30% w/w of the total weight of the composition; and reduced graphene oxide in an amount in the range of 70% to 80% w/w of the total weight of the composition to obtain naphthalenes and isoparaffins selectively more than 40%.

In an embodiment of the present disclosure, there is provided a process for producing a catalyst composition as described herein, wherein the catalyst composition is at least one heteropoly acid in an amount in the range of 15% to 85% w/w of the total weight of the composition, and support material in an amount in the range of 15% to 85% w/w of the total weight of the composition.

In an embodiment of the present disclosure, there is provided a process for isomerization of paraffins as described herein, wherein the at least one heteropoly acid is in an amount in the range of 15% to 30% w/w of the total weight of the composition.

In an embodiment of the present disclosure, there is provided a process for isomerization of paraffins as described herein, wherein the reduced graphene oxide is in an amount in the range of 70% to 85% w/w of the total weight of the composition.

In an embodiment of the present disclosure, there is provided a process for isomerization of paraffins as described herein, wherein the catalyst composition is 23-25% w/w tungstophosphoric acid (TPA), and 70-80% w/w reduced graphene oxide.

In an embodiment of the present disclosure, there is provided a process for isomerization of paraffins as described herein, wherein the at least one heteropoly acid is selected from the group consisting of tungstophosphoric acid (TPA), molybdophosphoric acid (MPA), and combinations thereof.

In an embodiment of the present disclosure, there is provided a process for isomerization of paraffins as described herein, wherein the at least one heteropoly acid has a general formula selected from the group consisting of $H_xA_y[BD_6O_{24}].zH_2O$, $H_xA_y[BD_{12}O_{40}].zH_2O$, $H_xA_y[B_2D_{18}O_{62}].zH_2O$, and $H_xA_y[B_5D_{30}O_{110}].zH_2O$, wherein A is selected from a group consisting of alkali metal, alkali earth metal, post transitional metal, ammonium salt, and phosphonium salt; B is selected from the group consisting of P, Si, As, Ge, and D; D is selected from the group consisting of Ti, V, Cr, Mn, Fe, Co, Ni, Cu, Zn, Ga, Zr, Nb, Mo, Tc, Rh, Cd, In, Sn, Ta, W, and Re.

In an embodiment of the present disclosure, there is provided a process for isomerization of paraffins as described herein, wherein the at least one heteropoly acid has a general formula $H_{3-y}A_yPW_{12}O_{40}$.

In an embodiment of the present disclosure, there is provided a process for isomerization of paraffins as described herein, wherein A is selected a group consisting of Li, Na, K, Rb, Cs, Mg, Ca, Al, ammonium salt, phosphonium salt, Pd, Ag, Ni, Al, and Cu.

In an embodiment of the present disclosure, there is provided a process for isomerization of paraffins as described herein, wherein the at least one heteropoly acid has a general formula $H_{3-y}A_yPW_{12}O_{40}$, and wherein y is 0 to 3.

In an embodiment of the present disclosure, there is provided a process for isomerization of paraffins as described herein, wherein the at least one heteropoly acid has a general formula $H_{3-y}A_yPW_{12}O_{40}$, and wherein y is 2.5.

In an embodiment of the present disclosure, there is provided a process for isomerization of paraffins as described herein, wherein the paraffin is a refinery feedstock such as straight run naphtha, cracked run naptha and fcc naphtha.

In an embodiment of the present disclosure, there is provided a process for isomerization of paraffins as described herein, wherein the paraffin is $C_5$ to $C_{10}$ linear paraffin.

In an embodiment of the present disclosure, there is provided a process for isomerization of paraffins as described herein, wherein hydrogen is passed over the catalyst composition at a rate of 10-100 mL/min.

In an embodiment of the present disclosure, there is provided a process for isomerization of paraffins as described herein, wherein feedstock is fed at a rate of 0.05 mL/min.

In an embodiment of the present disclosure, there is provided a process for isomerization of paraffins as described herein, wherein the process is carried out at a temperature in the range of 150-300° C.

In an embodiment of the present disclosure, there is provided a process for isomerization of paraffins as described herein, wherein the process is carried out at a temperature of 250° C.

In an embodiment of the present disclosure, there is provided a process for isomerization of paraffins as described herein, wherein the process is carried out at a pressure in the range of 5-50 bar.

In an embodiment of the present disclosure, there is provided a process for isomerization of paraffins as described herein, wherein the process is carried out at a pressure of 30 bar.

In an embodiment of the present disclosure, there is provided a process for isomerization of paraffins as described herein, wherein the paraffin weight hourly space velocity is in the range of 0.01 to 10 $hr^{-1}$.

In an embodiment of the present disclosure, there is provided a process for isomerization of paraffins as described herein, wherein the paraffin weight hourly space velocity is 2 $hr^{-1}$.

Although the subject matter has been described in considerable detail with reference to certain embodiments thereof, other embodiments are possible.

EXAMPLES

The following examples are given by way of illustration of the present invention and should not be construed to limit the scope of present disclosure. It is to be understood that both the foregoing general description and the following detailed description are exemplary and explanatory only and are intended to provide further explanation of the claimed subject matter.

Example 1

Preparation of rGO
Synthesis of Graphene Oxide (GO):
Graphene oxide was synthesized by improved synthesis of graphene oxide, a 9:1 mixture of concentrated $H_2SO_4$/$H_3PO_4$ (360:40 mL) was added to a mixture of graphite flakes (3.0 g, 1 wt equiv) with a purity of 99.8% was purchased from Sigma Aldrich. The mixture was and left for aging for 3 days. KMnO4 (18.0 g, 6 wt equiv) was added to the mixture post aging producing a slight exotherm to 35-40° C. The reaction was then heated to 50° C. and stirred for 48 h. The reaction was cooled to room temperature and poured onto ice (400 mL) with 30% $H_2O_2$ (3 mL) AR Grade. The mixture was filtered through polyester filter. The filtrate was centrifuged (8000 rpm for 15 min), and the supernatant was decanted away. The remaining solid material was then washed in succession with 200 mL of water, 200 mL of 30% HCl (37% fuming), and 200 mL of ethanol. The material remaining after this extended multiple-wash process was coagulated with 200 mL of ether. The solid obtained on the filter was vacuum-dried overnight at room temperature, obtaining 5.8 g of product.

Synthesis of Exfoliated Graphite Oxide (XGO):

Aqueous colloids of XGO were prepared by dispersing 1.0 g GO into 500 mL of distilled water by ultrasonication and centrifugation for 2 hr to remove any unexfoliated GO. The XGO was dried at 45° C. for 24 h.

Synthesis of Reduced Graphene Oxide (rGO):

The rGO was prepared by dispersing 400 mg XGO into 800 mL of distilled water and treating GO with hydrazine hydrate and maintaining the solution at 100° C. for 24 hours.

Example 2

Preparation of Composites

Figure 2:
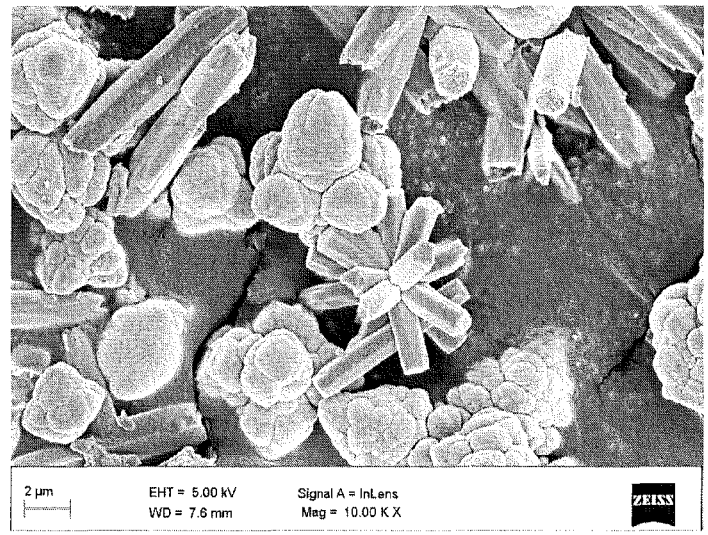
FIG. 2 depicts the scanning electron microscopy (SEM) image of molybdophosphoric acid (MPA) synthesized by hydrothermal route.

Following three methodologies were used to synthesize composites:

a) Conventional MPA synthesis: Phosphomolybdic acid was obtained by dissolving ammoniumheptamolybdate (AMH) in water, mixed slowly with dilute ortho-phosphoric acid solution such that a Mo/P ratio of 12 was maintained. Concentrated HCl was added drop wise to the above solution until the formation of yellow precipitate had stopped. The obtained yellow precipitate was dried overnight (12 h) at 100° C. and calcined at 350° C. for 4 hours. The SEM images shown in FIG. 1 indicate a cuboidal morphology. The SEM images shown in FIG. 2 indicate rosette morphology for this class of heteropoly acids upon hydrothermal treatment.

Figure 3:
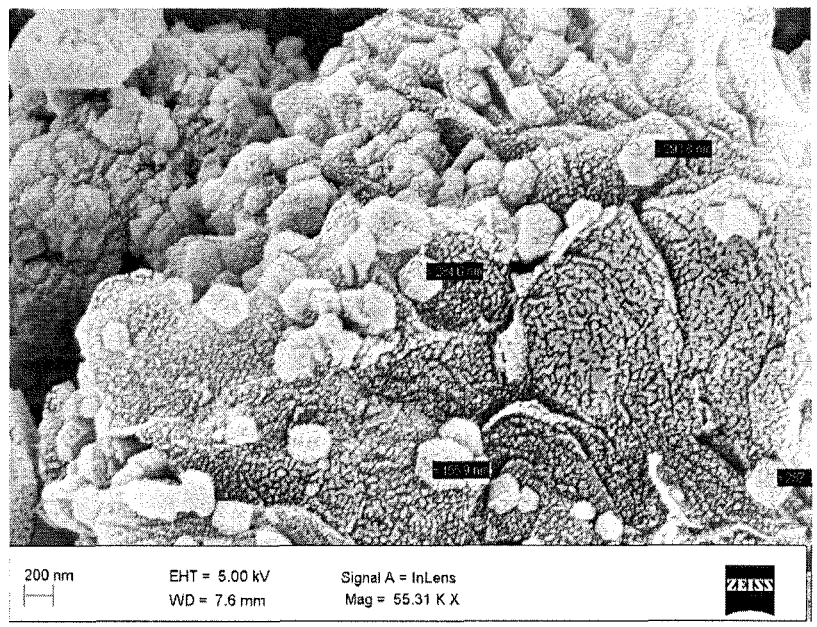
FIG. 3 depicts the scanning electron microscopic (SEM) image of molybdophosphoric acid (MPA) impregnated on reduced graphene oxide (rGO) at 25° C. without thermal treatment.
Figure 4:
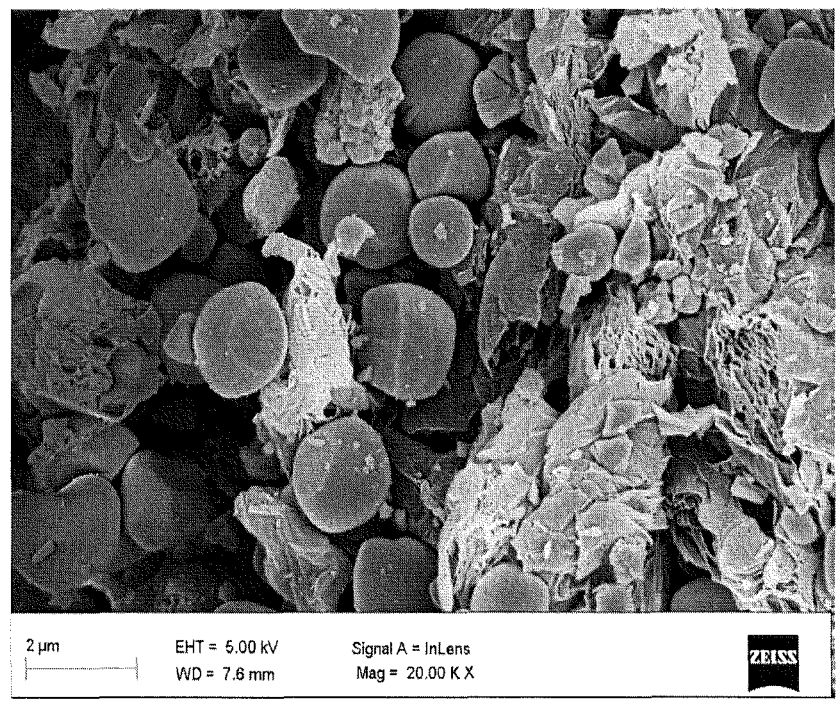
FIG. 4 depicts the scanning electron microscopy (SEM) image of molybdophosphoric acid (MPA) impregnated on reduced graphene oxide (rGO) subjected to thermal treatment.
Figure 5:
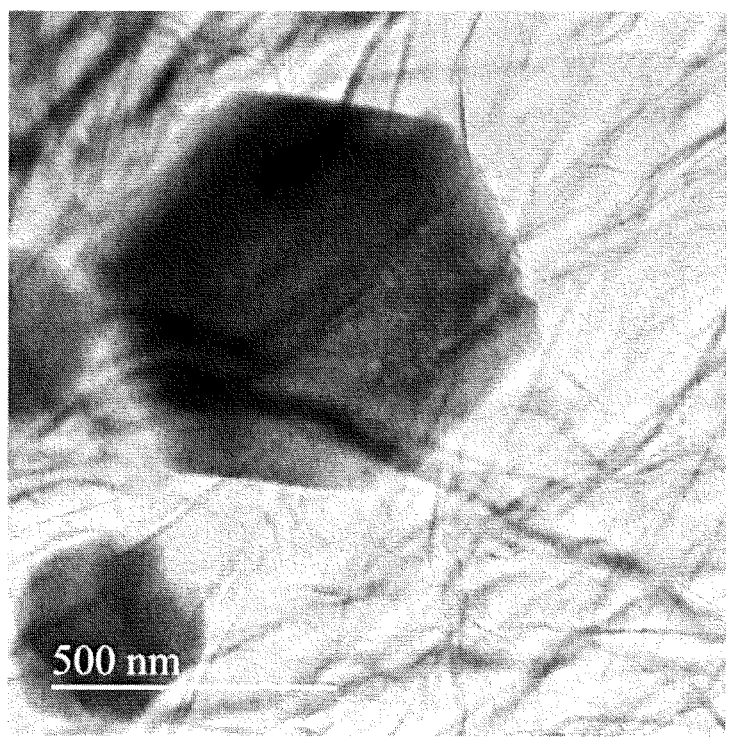
FIG. 5 depicts the transmission electron microscopy (TEM) image of molybdophosphoric acid (MPA) impregnated on reduced graphene oxide (rGO) subjected to thermal treatment.

(b) MPA was synthesized and impregnated on rGO followed by hydrothermal treatment. Phosphomolybdic acid (PMA) was impregnated over rGO by traditional wet impregnation method where a solution of rGO in water is mixed with as synthesized MPA under stirring for 2 hours at 25° C., and subsequently subjected to hydrothermal treatment at 85° C. for 12 hours. The final material was filtered and dried at 100° C. for 8 h. The SEM images shown in FIG. 3 indicate crystals were found to be embedded over the nano sheets of rGO. However, upon hydrothermal treatment, FIG. 4 indicates MPA crystals were found to be embedded within the nano sheets of rGO.

Figure 6:
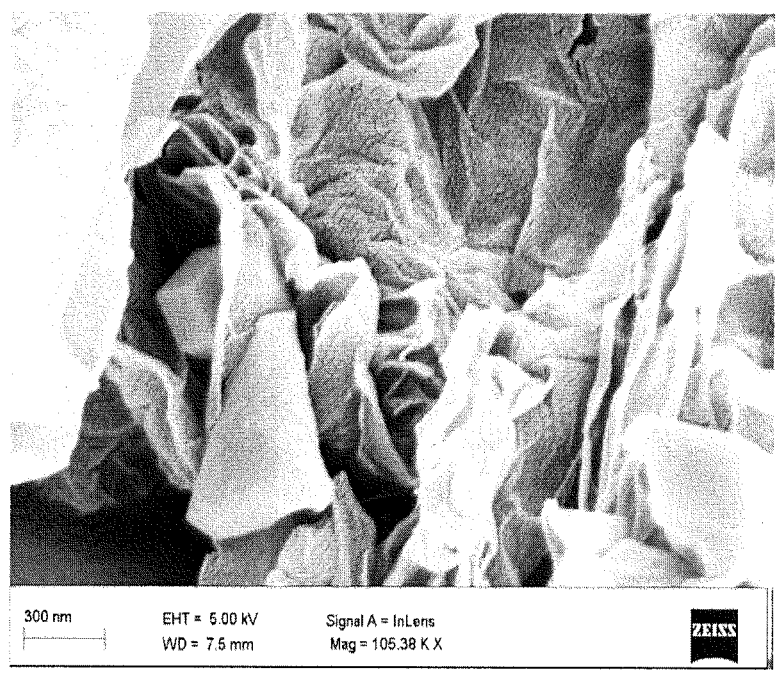
FIG. 6 depicts the scanning electron microscopic (SEM) image of reduced graphene oxide (rGO) assisted molybdophosphoric acid (MPA) synthesis post thermal treatment.
Figure 7:
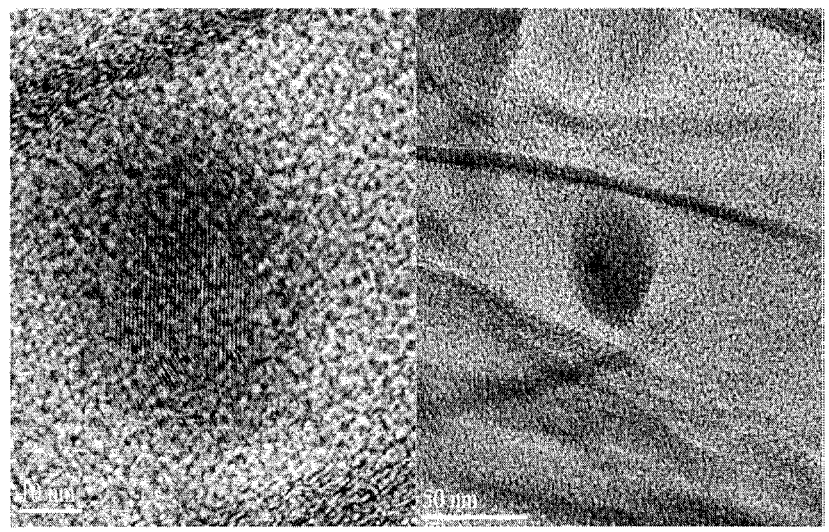
FIG. 7 depicts the transmission electron microscopic (TEM) image of reduced graphene oxide (rGO) assisted molybdophosphoric acid (MPA) synthesis subjected to thermal treatment.

(c) rGO Assisted MPA Synthesis: A dilute solution of AMH was impregnated on rGO prior to the conventional PMA synthesis. The solution was mixed slowly with dilute ortho-phosphoric acid solution such that a Mo/P ratio of 12 was maintained. Concentrated HCl was added drop wise to the above solution until the formation of yellow precipitate had stopped. Subsequently the mixture was subjected to hydrothermal treatment at 85° C. for 12 hours. The obtained greenish grey precipitate was dried overnight (12 h) at 100° C. and calcined at 350° C. for 4 hours. FIG. 6 indicates MPA crystals are embedded within the nano sheets of rGO as shown in the inset indicating the restricted morphological changes. FIG. 7 showing TEM images also confirm the embedding of MPA inside rGO sheets. Table 1 below details morphological features of different MPA-rGO composites synthesized with the aforementioned methods, wherein MPA stands for molybdophosphoric acid and rGO stands for reduced graphene oxide.

TABLE 1

| S. No. | Type | Temperature (° C.) | Observations (Morphological) |
|---|---|---|---|
| 1. | Pure MPA Synthesis | 25 | Hexagonal |
| 2. | Pure MPA Synthesis | 85 | Rosette |
| 3. | MPA Impregnated on rGO | 25 | Cuboidal |
| 4. | MPA Impregnated on rGO | 85 | Cuboidal embedded within sheets of rGO |
| 5. | rGO Assisted MPA Synthesis | 25 | Cuboidal embedded within sheets of rGO |
| 6. | rGO Assisted MPA Synthesis | 85 | Cuboidal particles embedded within sheets of rGO restricted the rosette morphology formation. |

Thus, MPA synthesized at lower temperature was found to have a hexagonal structure, which on thermal/hydrothermal treatments transformed to rosette morphology.

The cuboidal crystals of MPA impregnated on rGO were found to be cuboidal/hexagonal/spherical. However, thermal treatment of MPA impregnated on rGO did not result in rosette morphology.

The synthesis of MPA carried out with rGO as support with loading precursors in rGO resulted only in cuboidal/spherical/hexagonal crystals embedded within the rGO sheets confirmed by HRTEM, FESEM and elemental mapping. Further confirmation was obtained by carrying out the catalytic activity of paraffin isomerization. The presence of MPA within the nano sheets of rGO provides superior catalytic performance exhibited by metal-HPA-rGO composite compared to the control experiments (metal-rGO composite).

Example 3

Preparation of Metal-rGO Composite

Platinum was impregnated over rGO by traditional wet impregnation method where a solution of platinum salt (platinum nitrate; 0.029 g) in water (10 mL) is mixed with rGO (5 g) under stirring for 2 hours at 25° C., and subsequently subjected to thermal treatment at 200° C. for 4 hours. The final material was filtered and dried at 100° C. for 8 h to obtain CAT 1 with 0.3% of Pt and 100% of rGO.

Preparation of Metal—MPA—rGO Composite:

12-phosphotungstic acid (Aldrich) was dried at 100° C. to remove the physically adsorbed water before use. $Ni(NO_3)_2$ (Aldrich 99.9%) was used as received. $Ni_yH_{3-y}PW_{12}O_{40}$ samples (y=2.5) was prepared by drop wise addition of predetermined amounts of a $Ni(NO_3)_2$ aqueous on HPW at room temperature. A greenish white precipitate formed, and the solution was stirred for 2 h for uniform mixing. The solvent was vacuum dried and further left to dry overnight at room temperature evaporate the water. Fine greenish white powder was obtained by oven-drying the materials in air at 100° C. The powder was calcined at 300 degrees for 4 hrs. The synthesized Ni—HPW was impregnated by adding a known weight of Ni—HPW on the rGO support and stirred for 12 h at 85° C. The solution was vacuum dried and calcined at 300° C. for 4 h. Table 2 below details the composition of different catalyst composites of the present disclosure, wherein MPA stands for molybdophosphoric acid, HPA stands for heteropoly acid and rGO stands for reduced graphene oxide.

TABLE 2

| Sample No | Metal (Ni); Value of Y | Compound Ratio (Metal HPA):rGO | Type of HPA |
|---|---|---|---|
| CAT 2 | 2.5 | 3:10 | TPA |
| CAT 2 | 2.5 | 3:10 | TPA |
| CAT 3 | 2.5 | 3:10 | MPA |
| CAT 3 | 2.5 | 3:10 | MPA |

Preparation of Ni-TPA-rGO (CAT 2)

0.3784 g of nickel nitrate was dissolved in 10 ml distilled water. The solution was transferred to a round bottom flask containing 1.5 g of tungstophosphoric acid (TPA). This mixture has 0.07641 g of Ni which contributes to 4.0677% of total mixture of (0.3784 g of Nickel Nitrate+1.5 g of TPA=1.878 g total mixture). The round bottom flask was kept for stirring in the vacuum rotavapor BUCCI till the temperature of the bath attains 70° C. The solvent was evaporated from the sample using vacuum rotavapour. The dried sample was then calcined at 350° C. for 4 hours.

1.5 g of the above synthesized composite was dissolved in 10 ml of water (This mixture has 0.061005 g of Ni and 1.4349 g of TPA). This solution was transferred to a round bottom flask containing 5 g of rGO. This composite has 0.30226 g of Nickel Nitrate, 1.4349 g of TPA and 5 g of rGO contribute to 0.9385% Ni-22.075% TPA-76.9865% rGO. The round bottom flask was kept for stirring in the vacuum rotavapor BUCCI till the temperature of the bath attains 70° C. The solvent was evaporated from the sample using vacuum rotavapour. The dried sample was then calcined at 350° C. for 4 hours.

Catalyst formation: The catalysts were pelletized using a Retsch PP25 pellet press with 20 bar pressure. The pelletized catalysts were coarse ground to US Test Sieve 850/600 μm.

Preparation of Ni-MPA-rGO (CAT-3)

0.5974 g of nickel nitrate was dissolved in 10 ml distilled water. The solution was transferred to a round bottom flask containing 1.5 g of molybdophosphoric acid (MPA). This mixture has 0.12058 g of Ni which contributes to 5.749% of total mixture of (0.5974 g of nickel nitrate+1.5 g of TPA=2.094 g total mixture). The round bottom flask was kept for stirring in the vacuum rotavapor BUCCI till the temperature of the bath attains 70° C. The solvent was evaporated from the sample using vacuum rotavapour. The dried sample was then calcined at 350° C. for 4 hours.

1.5 g of the above synthesized composite was dissolved in 10 ml of water (This mixture has 0.0862 g of nickel nitrate and 1.4137 g of MPA). This solution was transferred to a round bottom flask containing 5 g of rGO. This composite has 0.0862 g of nickel nitrate, 1.4137 g of MPA and 5 g of rGO contribute to 1.853% Ni-21.749% MPA-78.2507% rGO. The round bottom flask was kept for stirring in the vacuum rotavapor BUCCI till the temperature of the bath attains 70° C. The solvent was evaporated from the sample using vacuum rotavapour. The dried sample was then calcined at 350° C. for 4 hours.

Catalyst formation: The catalysts were pelletized using a Retsch PP25 pellet press with 20 bar pressure. The pelletized catalysts were coarse ground to US Test Sieve 850/600 μm Example 4

Process for Isomerization of Paraffins

Table 3 below details the isomerizing activity of a reference catalyst, wherein TPA stands for tungstophosphoric acid and rGO stands for reduced graphene oxide.

TABLE 3

| Sample No | Metal (Pt/Ni); Value of Y | Compound Ratio (Metal HPA):rGO | Type of HPA | Catalyst | Composition | Composition in Weights 30% Tetraamine Platinum Nitrate/ Nickel Nitrate | HPA | 100% rGO | Temp. (° C.) | Conversion (%) | Isoparaffin Selectivity | Products formed |
|---|---|---|---|---|---|---|---|---|---|---|---|---|
| 1 | 0.2214 | 3:10 | — | CAT 1 | 0.3% Pt-100% rGO | 0.029772 | — | 5 | 250 | 5.02 | 32.072 | Isoparaffins 1.61 Olefins 0.07 Naphthenes 0.75 Aromatics 2.58 |
| 2 | 2.5 | 3:10 | TPA | CAT2 | 1.1% Ni - 22.8% PTA - 76% rGO | 1.2621 | 5 | 5 | 250 | 54.01 | 74.13 | Isoparaffins 40.04 Olefins 0.33 Naphthenes 13.33 Aromatics 0.3 |
| 3 | 2.5 | 3:10 | MPA | CAT3 | 1.1% Ni - 22.8% PMA - 76% rGO | 1.995 g | 5 | 5 | 250 | 18.49 | 91.08 | Isoparaffins 16.84 Olefins 0.11 Naphthenes 1.05 Aromatics 0.48 |

All catalysts were first reduced under a hydrogen flow of 35 ml/min at a temperature of 300° C. and atmospheric pressure. All catalytic evaluations were done after the reduction step in a fixed bed reactor at a temperature of 250° C., a pressure of 30 bar and under hydrogen flow of 35 ml/min and a nitrogen flow of 10 ml/min.

CAT1 has shown the least conversion at a value of 5.02% and only a 32% selectivity towards isomerization. Without being bound by theory, it is suggested that the low conversion and selectivity may be due to the presence of functional groups on the surface of reduced graphene oxide. CAT2, surprisingly, exhibits a conversion of 54.01% and a selectivity of 74.13% towards isomers. TPA is a highly acidic material and loading this material on rGO has increased the acidity of the composite altogether which explains the high activity of this catalyst compared to other catalysts. Surprisingly, CAT 2 shows significant selectivity towards naphthenes thereby leading to a decrease in selectivity towards isoparaffins. CAT3 has shown a conversion of 18.49 and a selectivity of 91.08% towards isomerization. Surprisingly, the activity of CAT3 is lesser than activity of CAT2, however, PMA has shown a better selectivity towards isomerization and naphthenes are formed only to an extent of 1.05% on this catalyst. This behavior can be explained due to the moderate acidity of this material as compared to CAT2.

Although the subject matter has been described in considerable detail with reference to certain examples and implementations thereof, other implementations are possible. As such, the spirit and scope of the appended claims should not be limited to the description of the preferred examples and implementations contained therein.

What is claimed is:

1. A catalyst composition comprising:
   at least one heteropoly acid; and reduced graphene oxide, said at least one heteropoly acid selected from the group consisting of tungstophosphoric acid (TPA), molybdophosphoric acid (MPA), and combinations thereof and said at least one heteropoly acid being present in said catalyst composition at an amount of from 15% to 85% by weight based on a total weight of the composition.

2. The catalyst composition as claimed in claim 1, wherein said at least one heteropoly acid is present in an amount in the range of 15% to 30% by weight based on the total weight of the composition.

3. The catalyst composition as claimed in claim 1, wherein the reduced graphene oxide is present in an amount in the range of 15% to 85% by weight based on the total weight of the composition.

4. The catalyst composition as claimed in claim 1, wherein the catalyst is used for isomerization of paraffins.

5. A process for producing a catalyst composition as claimed in claim 1, the process comprising;
   contacting at least one heteropoly acid with reduced graphene oxide to obtain a first solution;
   stirring the first solution for to obtain a second solution;
   drying the second solution to obtain a dried paste;
   calcining the dried paste to obtain a catalyst composition.

6. The process as claimed in claim 5, wherein the first solution is stirred for 8-20 hours at 70-100° C.

7. The process as claimed in claim 5, wherein the dried paste is calcined at 200-400° C. for a period of 2-6 hours.

* * * * *